(12) United States Patent
Omenetto et al.

(10) Patent No.: US 10,040,834 B2
(45) Date of Patent: Aug. 7, 2018

(54) BIOPOLYMER OPTOFLUIDIC DEVICE AND METHOD OF MANUFACTURING THE SAME

(71) Applicant: TUFTS UNIVERSITY, Medford, MA (US)

(72) Inventors: Fiorenzo Omenetto, Lexington, MA (US); David L. Kaplan, Concord, MA (US); Brian Lawrence, New York, NY (US); Mark Cronin-Golomb, Reading, MA (US)

(73) Assignee: TUFTS UNIVERSITY, Medford, MA (US)

( * ) Notice: Subject to any disclaimer, the term of this patent is extended or adjusted under 35 U.S.C. 154(b) by 677 days.

(21) Appl. No.: 14/154,134

(22) Filed: Jan. 13, 2014

(65) Prior Publication Data

US 2014/0349380 A1 Nov. 27, 2014

Related U.S. Application Data

(63) Continuation of application No. 12/513,423, filed as application No. PCT/US2007/083634 on Nov. 5, 2007.

(Continued)

(51) Int. Cl.
*G02B 1/06* (2006.01)
*G01N 33/543* (2006.01)
(Continued)

(52) U.S. Cl.
CPC ........ *C07K 14/43586* (2013.01); *B29C 39/02* (2013.01); *B29D 11/0074* (2013.01);
(Continued)

(58) Field of Classification Search
CPC . G02B 1/06; G02B 1/04; G02B 6/138; G02B 6/12; G01N 33/543; B29D 11/00; B29C 39/02; B82Y 20/00
See application file for complete search history.

(56) References Cited

U.S. PATENT DOCUMENTS 4,676,640 A 6/1987 Briggs
4,977,902 A 12/1990 Sekino et al.
(Continued)

FOREIGN PATENT DOCUMENTS

EP 0245509 A1 11/1987
EP 1025988 A1 8/2000
(Continued)

OTHER PUBLICATIONS

Anderson, J. et al., Bioactive Silk-Like Protein Polymer Films on Silicon Devices, Materials Research Society Synthesis and Thermoelectric Properties, 330:171-177 (1994).
(Continued)

*Primary Examiner* — Nahida Sultana
(74) *Attorney, Agent, or Firm* — Quarles & Brady, LLP

(57) ABSTRACT

A method of manufacturing a biopolymer optofluidic device including providing a biopolymer, processing the biopolymer to yield a biopolymer matrix solution, providing a substrate, casting the biopolymer matrix solution on the substrate, embedding a channel mold in the biopolymer matrix solution, drying the biopolymer matrix solution to solidify biopolymer optofluidic device, and extracting the embedded channel mold to provide a fluidic channel in the solidified biopolymer optofluidic device. In accordance with another aspect, an optofluidic device is provided that is made of a biopolymer and that has a channel therein for conveying fluid.

11 Claims, 5 Drawing Sheets

Related U.S. Application Data

(60) Provisional application No. 60/856,297, filed on Nov. 3, 2006.

(51) Int. Cl.

| | | |
|---|---|---|
| *C07K 14/435* | (2006.01) | |
| *B29C 39/02* | (2006.01) | |
| *B29D 11/00* | (2006.01) | |
| *G02B 1/04* | (2006.01) | |
| *G02B 6/138* | (2006.01) | |
| *D01F 4/02* | (2006.01) | |
| *G01N 33/544* | (2006.01) | |
| *B82Y 20/00* | (2011.01) | |
| *G02B 6/12* | (2006.01) | |
| *G02B 1/00* | (2006.01) | |
| *G02B 5/18* | (2006.01) | |

(52) U.S. Cl.
CPC .......... *B29D 11/00663* (2013.01); *D01F 4/02* (2013.01); *G01N 33/544* (2013.01); *G01N 33/5436* (2013.01); *G01N 33/54373* (2013.01); *G01N 33/54386* (2013.01); *G02B 1/04* (2013.01); *G02B 1/046* (2013.01); *G02B 1/06* (2013.01); *G02B 6/138* (2013.01); *B82Y 20/00* (2013.01); *D10B 2211/04* (2013.01); *D10B 2401/20* (2013.01); *G01N 2333/43578* (2013.01); *G02B 1/005* (2013.01); *G02B 1/041* (2013.01); *G02B 1/045* (2013.01); *G02B 5/18* (2013.01); *G02B 2006/1213* (2013.01); *G02B 2006/12102* (2013.01); *G02B 2006/12104* (2013.01); *G02B 2006/12107* (2013.01); *G02B 2006/12171* (2013.01)

(56) References Cited

U.S. PATENT DOCUMENTS

| | | | |
|---|---|---|---|
| 4,999,295 A | 3/1991 | Asakura et al. | |
| 5,244,799 A | 9/1993 | Anderson | |
| 5,252,285 A | 10/1993 | Lock | |
| 5,427,096 A | 6/1995 | Bogusiewicz et al. | |
| 5,474,915 A | 12/1995 | Dordick et al. | |
| 5,512,218 A | 4/1996 | Gresser et al. | |
| 5,552,270 A | 9/1996 | Khrapko et al. | |
| 6,134,045 A | 10/2000 | Jiang et al. | |
| 6,150,491 A | 11/2000 | Akkara | |
| 6,284,418 B1 | 9/2001 | Trantolo | |
| 6,489,446 B1 | 12/2002 | Rothstein et al. | |
| 6,753,064 B1 | 6/2004 | Nakama et al. | |
| 6,753,131 B1 | 6/2004 | Rogers et al. | |
| 6,924,503 B2 | 8/2005 | Cheng et al. | |
| 6,989,897 B2 | 1/2006 | Chan et al. | |
| 6,992,325 B2 | 1/2006 | Huang | |
| 7,162,127 B2* | 1/2007 | Ohtsu | G02B 6/1221 250/227.11 |
| 7,223,609 B2 | 5/2007 | Anvar et al. | |
| 7,267,958 B2 | 9/2007 | Dordick et al. | |
| 7,427,371 B2* | 9/2008 | Kawanishi | B23H 9/04 219/69.11 |
| 7,476,398 B1 | 1/2009 | Doillon et al. | |
| 7,498,802 B2 | 3/2009 | Takahata | |
| 7,674,882 B2 | 3/2010 | Kaplan et al. | |
| 7,713,778 B2 | 5/2010 | Li et al. | |
| 7,828,997 B2* | 11/2010 | Otoshi | B29C 47/0021 264/1.31 |
| 8,005,526 B2 | 8/2011 | Martin et al. | |
| 8,348,974 B2 | 1/2013 | Asakura | |
| 8,529,835 B2* | 9/2013 | Kaplan | B29D 11/0074 422/50 |
| 8,563,329 B2* | 10/2013 | Yin | B82Y 5/00 422/407 |
| 8,663,909 B2* | 3/2014 | Gazenko | C12Q 1/04 435/174 |
| 8,666,471 B2* | 3/2014 | Rogers | A61B 5/05 600/373 |
| 8,715,740 B2* | 5/2014 | Wang | A61K 9/5169 264/4.1 |
| 8,722,067 B2* | 5/2014 | Wang | A61K 9/5089 424/400 |
| 8,747,886 B2* | 6/2014 | Amsden | B82Y 10/00 424/443 |
| 9,171,794 B2* | 10/2015 | Rafferty | H01L 23/4985 |
| 9,513,405 B2 | 12/2016 | Kaplan et al. | |
| 9,802,374 B2 | 10/2017 | Kaplan et al. | |
| 2001/0002417 A1 | 5/2001 | Akkara et al. | |
| 2001/0003043 A1 | 6/2001 | Metspalu et al. | |
| 2003/0020915 A1 | 1/2003 | Schueller et al. | |
| 2003/0162696 A1 | 8/2003 | Mihara | |
| 2003/0203366 A1* | 10/2003 | Lim | G01N 33/54386 506/9 |
| 2003/0214057 A1 | 11/2003 | Huang | |
| 2004/0001299 A1 | 1/2004 | van Haaster et al. | |
| 2004/0029241 A1 | 2/2004 | Hahn et al. | |
| 2004/0081384 A1 | 4/2004 | Datesman et al. | |
| 2004/0229349 A1 | 11/2004 | Daridon | |
| 2004/0266992 A1 | 12/2004 | Migliaresi et al. | |
| 2005/0008675 A1 | 1/2005 | Bhatia et al. | |
| 2005/0151966 A1 | 7/2005 | Packirisamy et al. | |
| 2005/0164920 A1 | 7/2005 | Doherty et al. | |
| 2005/0169962 A1 | 8/2005 | Bhatia et al. | |
| 2005/0194365 A1 | 9/2005 | Li | |
| 2005/0208469 A1 | 9/2005 | Daunert et al. | |
| 2005/0213868 A1 | 9/2005 | Cunningham | |
| 2005/0217990 A1 | 10/2005 | Sibbett et al. | |
| 2005/0276791 A1 | 12/2005 | Hansford et al. | |
| 2006/0024813 A1 | 2/2006 | Warthoe | |
| 2006/0042822 A1 | 3/2006 | Azeyanagi et al. | |
| 2006/0091571 A1 | 5/2006 | Akutsu et al. | |
| 2006/0111517 A1 | 5/2006 | Feucht et al. | |
| 2006/0134606 A1 | 6/2006 | Montagu | |
| 2006/0141617 A1 | 6/2006 | Desai et al. | |
| 2006/0159837 A1 | 7/2006 | Kaplan et al. | |
| 2006/0177479 A1 | 8/2006 | Giachelli et al. | |
| 2006/0178655 A1 | 8/2006 | Santini et al. | |
| 2006/0205927 A1 | 9/2006 | Jin et al. | |
| 2006/0226575 A1 | 10/2006 | Maghribi et al. | |
| 2006/0236436 A1 | 10/2006 | Li et al. | |
| 2007/0007661 A1 | 1/2007 | Burgess et al. | |
| 2007/0009968 A1 | 1/2007 | Cunningham et al. | |
| 2007/0026064 A1 | 2/2007 | Yoder et al. | |
| 2007/0031607 A1 | 2/2007 | Dubson et al. | |
| 2007/0042505 A1 | 2/2007 | Israel et al. | |
| 2007/0058254 A1 | 3/2007 | Kim | |
| 2007/0073130 A1 | 3/2007 | Finch et al. | |
| 2007/0113355 A1 | 5/2007 | Knight | |
| 2007/0178240 A1 | 8/2007 | Yamazaki et al. | |
| 2007/0187862 A1 | 8/2007 | Kaplan et al. | |
| 2007/0214520 A1 | 9/2007 | Scheibel et al. | |
| 2007/0224677 A1 | 9/2007 | Neumann | |
| 2007/0233208 A1 | 10/2007 | Kurtz et al. | |
| 2007/0275030 A1 | 11/2007 | Muratoglu et al. | |
| 2008/0019925 A1 | 1/2008 | Begleiter | |
| 2008/0038236 A1 | 2/2008 | Gimble et al. | |
| 2008/0085272 A1 | 4/2008 | Kaplan et al. | |
| 2008/0152281 A1 | 6/2008 | Lundquist et al. | |
| 2008/0203431 A1 | 8/2008 | Garcia et al. | |
| 2008/0239755 A1 | 10/2008 | Parker et al. | |
| 2008/0288037 A1 | 11/2008 | Neysmith et al. | |
| 2009/0028910 A1 | 1/2009 | DeSimone et al. | |
| 2009/0171467 A1 | 7/2009 | Mann et al. | |
| 2009/0202614 A1 | 8/2009 | Kaplan et al. | |
| 2009/0208555 A1 | 8/2009 | Kuttler et al. | |
| 2009/0263430 A1 | 10/2009 | Scheibel et al. | |
| 2010/0028451 A1 | 2/2010 | Kaplan et al. | |
| 2010/0046902 A1 | 2/2010 | Kaplan et al. | |
| 2010/0063404 A1 | 3/2010 | Kaplan et al. | |
| 2010/0068740 A1 | 3/2010 | Kaplan et al. | |
| 2010/0070068 A1 | 3/2010 | Kaplan et al. | |
| 2010/0100975 A1 | 4/2010 | Sutherland et al. | |
| 2010/0120116 A1 | 5/2010 | Kaplan et al. | |

(56) References Cited

U.S. PATENT DOCUMENTS

| | | | |
|---|---|---|---|
| 2011/0135697 A1 | 6/2011 | Omenetto et al. | |
| 2012/0034291 A1 | 2/2012 | Amsden et al. | |
| 2013/0243693 A1* | 9/2013 | Omenetto | A61Q 17/04 424/9.1 |
| 2013/0323811 A1 | 12/2013 | Kaplan et al. | |
| 2014/0205797 A1 | 7/2014 | Kaplan et al. | |
| 2016/0376331 A1 | 12/2016 | Kaplan et al. | |

FOREIGN PATENT DOCUMENTS

| | | |
|---|---|---|
| EP | 1116987 A2 | 7/2001 |
| EP | 1166987 A2 | 1/2002 |
| EP | 1209280 A2 | 5/2002 |
| EP | 1467224 A1 | 10/2004 |
| JP | 60-142259 A | 7/1985 |
| JP | 60-155129 A | 8/1985 |
| JP | H01-135853 A | 5/1989 |
| JP | 01280242 A | 11/1989 |
| JP | H02-86799 A | 3/1990 |
| JP | 11042106 A | 2/1999 |
| JP | H11-123791 A | 5/1999 |
| JP | H11-183854 A | 7/1999 |
| JP | 2000-019119 A | 1/2000 |
| JP | 2000-096490 A | 4/2000 |
| JP | 2000-143472 A | 5/2000 |
| JP | 2000-180969 A | 6/2000 |
| JP | 2001-147301 A | 5/2001 |
| JP | 2001280242 A | 10/2001 |
| JP | 2002-287377 A | 10/2002 |
| JP | 2003-195001 A | 7/2003 |
| JP | 2003-322729 A | 11/2003 |
| JP | 2004162209 A | 6/2004 |
| JP | 2004-307661 A | 11/2004 |
| JP | 2005/031724 A | 2/2005 |
| JP | 2005-530983 A | 10/2005 |
| JP | 2006-119424 A | 5/2006 |
| JP | 2006241450 A | 9/2006 |
| JP | 2011-123791 A | 6/2011 |
| JP | 05-039368 B2 | 10/2012 |
| KR | 20060027113 A | 3/2006 |
| KR | 20070060822 A | 6/2007 |
| KR | 20080069553 A | 7/2008 |
| WO | WO-1993/015244 A1 | 8/1993 |
| WO | WO-96/05510 A2 | 2/1996 |
| WO | WO-2000/31752 A2 | 6/2000 |
| WO | WO-01/10464 A1 | 2/2001 |
| WO | WO-2001/85637 A2 | 11/2001 |
| WO | WO-03/038033 A2 | 5/2003 |
| WO | WO-04/000915 A2 | 12/2003 |
| WO | WO-2004/071949 A2 | 8/2004 |
| WO | WO-2004/092250 A1 | 10/2004 |
| WO | WO-05/012606 A2 | 2/2005 |
| WO | WO-2005/019503 A2 | 3/2005 |
| WO | WO-05/031724 A1 | 4/2005 |
| WO | WO-2005/103670 A1 | 11/2005 |
| WO | WO-05/123114 A2 | 12/2005 |
| WO | WO-2006/020507 A1 | 2/2006 |
| WO | WO-2008/004356 A1 | 1/2008 |
| WO | WO-2008/118211 A2 | 10/2008 |
| WO | WO-2008/127402 A2 | 10/2008 |
| WO | WO-2008/127403 A2 | 10/2008 |
| WO | WO-2008/127404 A2 | 10/2008 |
| WO | WO-2008/127405 A2 | 10/2008 |
| WO | WO-2008/140562 A2 | 11/2008 |
| WO | WO-2009/061823 A1 | 5/2009 |
| WO | WO-2010/042798 A2 | 4/2010 |
| WO | WO-2010059963 A2 | 5/2010 |
| WO | WO-2010/126640 A2 | 11/2010 |

OTHER PUBLICATIONS

Bai, J. et al., Regenerated spider silk as a new biomaterial for MEMS, Biomed Microdevices, 8:317-323 (2006).
Chrisey, D.B. et al., Laser Deposition of Polymer and Biomaterial Films, Chem. Rev 103(2):553-576 (2003).
Extended European Search Report for EP 09767706.6, 6 pages (dated Jan. 8, 2013).
Extended European Search Report for EP 13156510.3, 7 pages (dated Oct. 11, 2013).
Extended European Search Report for EP 13156523.6, 9 pages (dated Dec. 18, 2013).
Fukuoka T. et al., Enzymatic Polymerization of Tyrosine Derivatives. Peroxidase- and Protease-Catalyzed Synthesis of Poly(tyrosine)s with Different Structures, Biomacromolecules 3(4):768-774 (2002).
International Search Report for PCT/US2007/083600, 3 pages (dated Nov. 5, 2008).
International Search Report for PCT/US2007/083620, 3 pages (dated Dec. 5, 2008).
International Search Report for PCT/US2007/083634, 3 pages (dated Nov. 5, 2008).
International Search Report for PCT/US2007/083642, 3 pages (dated Nov. 5, 2008).
International Search Report for PCT/US2007/083646, 4 pages (dated Dec. 15, 2008).
International Search Report for PCT/US2011/032195, 3 pages (dated Oct. 27, 2011).
International Search Report of PCT/US2007/083605, dated Dec. 15, 2008, 6 pages.
International Search Report of PCT/US2007/083639, dated Dec. 12, 2008, 5 pages.
International Search Report of PCT/US2008/082487, dated Feb. 27, 2009, 3 pages.
International Search Report of PCT/US2009/047751, dated Feb. 2, 2010, 3 pages.
International Search Report of PCT/US2010/022701, dated Mar. 31, 2010, 2 pages.
International Search Report of PCT/US2010/024004, dated Nov. 26, 2010, 5 pages.
International Search Report of PCT/US2010/042585, dated May 25, 2011, 8 pages.
International Search Report of PCT/US2010/047307, dated Apr. 28, 2011, 3 pages.
International Search Report of PCT/US2010/050468, dated Jan. 6, 2011, 3 pages.
International Search Report of PCT/US2011/028094, dated Jul. 14, 2011, 4 pages.
International Search Report of PCT/US2011/041002, 4 pages (dated Feb. 29, 2012).
IPRP for PCT/US2007/083642, 6 pages (dated May 5, 2009).
IPRP of PCT/US2007/083600, dated May 5, 2009, 6 pages.
IPRP of PCT/US2007/083605, dated May 5, 2009, 10 pages.
IPRP of PCT/US2007/083620, dated May 5, 2009, 6 pages.
IPRP of PCT/US2007/083634, dated May 5, 2009, 6 pages.
IPRP of PCT/US2007/083639, dated May 5, 2009, 6 pages.
IPRP of PCT/US2007/083646, dated May 5, 2009, 10 pages.
IPRP of PCT/US2008/082487, dated May 11, 2010, 10 pages.
IPRP of PCT/US2009/047751, dated Dec. 18, 2010, 5 pages.
IPRP of PCT/US2010/022701, dated Aug. 2, 2011, 5 pages.
IPRP of PCT/US2010/024004, dated Aug. 16, 2011, 6 pages.
IPRP of PCT/US2010/042585, dated Jan. 24, 2012, 6 pages.
IPRP of PCT/US2010/047307, dated Mar. 6, 2012, 5 pages.
Jiang, W. et al, Silicon and Polymer Nanophotonic Devices Based on Photonic Crystals, Proceedings of the International Society of Optical Engineering, 6124(1):612410-1(2006).
Jin, H.J. et al., Water-Stable Silk Films with Reduced β-Sheet Content, Advanced Functional Materials, 15:1241-1247 (2005).
Joglekar, A.P. et al., A study of the deterministic character of optical damage by femtosecond laser pulses and applications to nanomachining, Appl. Phys. B., 77: 25-30 (2003).
Kouba et al., Fabrication of Nanoimprint Stamps for Photonic Crystals, Journal of Physics: Conference Series, 34(1):897-903 (2006).
Lawrence, B.D. et al., Bioactive silk protein biomaterial systems for optical devices, Biomacromolecules, 9:1214-1220 (2008).

(56) References Cited

OTHER PUBLICATIONS

Liu, Y. et al., 3D femtosecond laser patterning of collagen for directed cell attachment, Biomaterials, 26(22):4597-605 (2005).
Min, B.M. et al., Regenerated Silk Fibroin Nanofibers: Water Vapor-Induced Structural Changes and Their Effects on the Behavior of Normal Human Cells, Macromol. Biosci., 6(4):285-292 (2006).
Minoura, N. et al., Attachment and Growth of Cultured Fibroblast Cells on Silk Protein Matrices, J. Biomed. Mater. Res. 29(10):1215-1221 (1995).
Notification of Transmittal of International Search Report and the Written Opinion of PCT/US2011/032195, dated Oct. 27, 2011, 2 pages.
Partial European Search Report for EP 13156523.6, 6 pages (dated Aug. 28, 2013).
Ramanujam, P.S., Optical Fabrication of Nano-Structured Biopolymer Surfaces, Opt. Mater. 27:1175-1177 (2005).
Tamada, Y., New Process to Form a Silk Fibroin Porous 3-D Structure, Biomacromolecules, 6:3100-3106 (2005).
Tu, D. et al., A ZEP520-LOR Bilayer Resist Lift-Off Process by E-Beam Lithography for Nanometer Pattern Transfer, Proceedings of the 7th IEEE Conference on Nanotechnology, 624-627 (2007).
Verma, M.K. et al., Embedded Template-Assisted Fabrication of Complex Microchannels in PDMS and Design of a Microfluidic Adhesive, Langmuir, 22(24)10291-10295 (2006).
Wang, L. et al., Fabrication of Polymer Photonic Crystal Superprism Structures Using Polydimethylsiloxane Soft Molds Journal of Applied Physics, 101(11):114316/1-6 (2007).
Wang, X. et al., Biomaterial coatings by stepwise deposition of silk fibroin, Langmuir, 21(24):11335-41 (2005).
Written Opinion for PCT/US2011/032195, 5 pages (dated Oct. 27, 2011).
Written Opinion for PCT/US2007/083600, 5 pages (dated Nov. 5, 2008).
Written Opinion for PCT/US2007/083620, 5 pages (dated Dec. 5, 2008).
Written Opinion for PCT/US2007/083634, dated Nov. 5, 2008 (5 pages).
Written Opinion for PCT/US2007/083642, 5 pages (dated Nov. 5, 2008).
Written Opinion for PCT/US2007/083646, 9 pages (dated Dec. 15, 2008).
Written Opinion of PCT/US2007/083605, dated Dec. 15, 2008, 9 pages.
Written Opinion of PCT/US2008/082487, dated Feb. 27, 2009, 9 pages.
Written Opinion of PCT/US2009/047751, dated Feb. 2, 2010, 4 pages.
Written Opinion of PCT/US2010/022701, dated Mar. 31, 2010, 4 pages.
Written Opinion of PCT/US2010/024004, dated Nov. 26, 2010, 5 pages.
Written Opinion of PCT/US2010/042585, dated May 25, 2011, 5 pages.
Written Opinion of PCT/US2010/047307, dated Apr. 28, 2011, 4 pages.
Xu, P. and Kaplan, D.L., Horseradish peroxidase catalyzed polymerization of tyrosine derivatives for nanoscale surface patterning, Journal of Macromolecular Science, Part A: Pure and Applied Chemistry, 41(12):1437-1445 (2004).
Yang, L.J. et al., Fabrication of SU-8 embedded microchannels with circular cross-section, International Journal of Machine Tools & Manufacturing, 44:1109-1114 (2004).
Whitesides, G. M. et al, Soft Lithography in Biology and Biochemistry, Annu. Rev. Biomed. Eng., 3:335-73 (2001).

\* cited by examiner

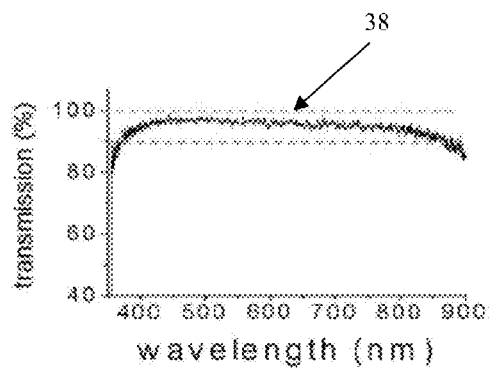
FIG. 3C
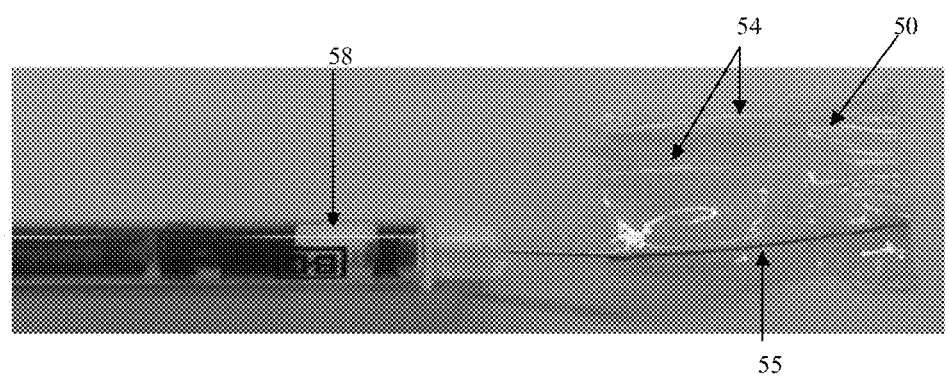
FIG. 4
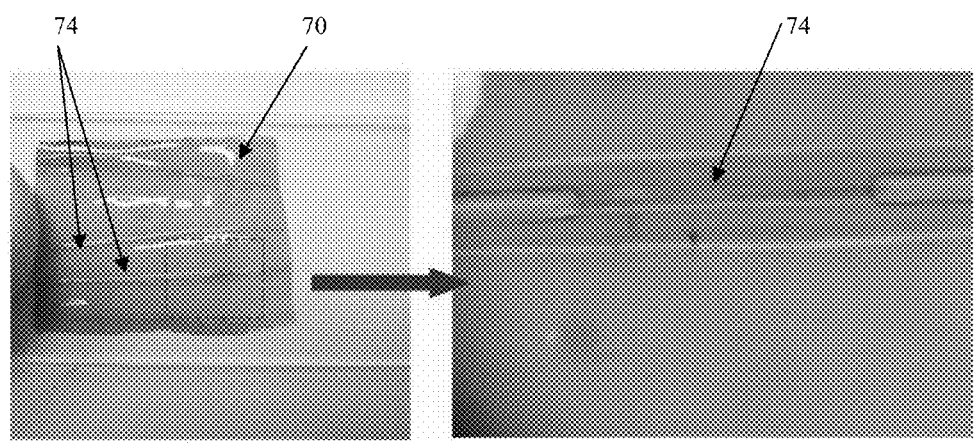
FIG. 5A                    FIG. 5B

BIOPOLYMER OPTOFLUIDIC DEVICE AND METHOD OF MANUFACTURING THE SAME

CROSS-REFERENCE TO RELATED APPLICATIONS

This application is a Continuation of U.S. patent application Ser. No. 12/513,423 filed on May 4, 2009, entitled "Biopolymer Optofluidic Device and Method of Manufacturing the Same" (incorporated herein by reference in its entirety), which is a National Stage Entry of International Patent Application No. PCT/US2007/083634 filed Nov. 5, 2007 (incorporated herein by reference in its entirety), and claims the benefit of priority of U.S. Provisional Application Ser. No. 60/856,297 filed on Nov. 3, 2006, entitled "Biopolymer Devices and Methods for Manufacturing the Same" (incorporated herein by reference in its entirety).

GOVERNMENT SUPPORT

The invention was made with government support under grant numbers EB002520 awarded by the National Institutes of Health, DMR0402849 awarded by the National Science Foundation, and FA9550-04-1-0363 awarded by the United States Air Force. The government has certain rights in this invention.

BACKGROUND OF THE INVENTION

Field of the Invention

The present invention is directed to biopolymer optofluidic devices, and methods for manufacturing such devices.

Description of Related Art

The field of optics is well established. Some subfields of optics include diffractive optics, micro-optics, photonics and guided wave optics. Various optical devices have been fabricated in these and other subfields of optics for research and commercial application. For example, common optical devices include lenses, diffraction gratings, photonic crystals, waveguides, optofluidic devices, etc. Optofluidics specifically refers to a class of adaptive optical circuits that integrate optical and fluidic devices together. Optofluidic devices are optical devices that incorporate one or more fluidic channels to convey fluid through the device. In this regard, optofluidic devices can be lenses, diffraction gratings, photonic crystals, waveguides, and the like. The introduction of liquids in the optical structure enables flexible fine-tuning of the optical device, and even allows reconfiguration of optical circuits such that they perform tasks optimally in a changing environment. An overview of optofluidics is available at Caltech's website: http://optofluidics.caltech.edu/optofluidics/index.html.

Optical devices and optofluidic devices are fabricated using various methods depending on the application and optical characteristics desired. However, these devices, and the fabrication methods employed in their manufacture, generally involve significant use of non-biodegradable materials. For example, glass, fused silica, and plastic are commonly used. Such materials are not biodegradable and remain in the environment for extended periods of time after the optical and optofluidic devices are removed from service and discarded. Of course, some of the materials can be recycled and reused. However, recycling also requires expenditures of natural resources and adds to the environmental costs associated with such materials.

Therefore, there exists an unfulfilled need for optofluidic devices that minimize the negative impact to the environment. In addition, there exists an unfulfilled need for optofluidic devices that provide additional functional features that are not provided by conventional optofluidic devices.

SUMMARY OF THE INVENTION

In view of the foregoing, objects of the present invention are to provide optofluidic devices that are made from a biopolymer and to provide methods for manufacturing such optofluidic devices that may be used in various applications.

One aspect of the present invention is to provide biopolymer optofluidic devices.

Another aspect of the present invention is to provide a method for manufacturing such biopolymer optofluidic devices.

One advantage of the present invention is in providing optofluidic devices that minimize the negative impact to the environment.

Another advantage of the present invention is in providing optofluidic devices that are biocompatible.

Yet another advantage of the present invention is in providing biopolymer optofluidic devices that have additional functional features that are not provided by conventional optofluidic devices.

In the above regard, inventors of the present invention recognized that biopolymers, and especially silk proteins, present novel structure and resulting functions. For example, from a materials science perspective, silks spun by spiders and silkworms represent the strongest and toughest natural fibers known and present various opportunities for functionalization, processing, and biocompatibility. Over five millennia of history accompany the journey of silk from a sought-after textile to a scientifically attractive fiber. As much as its features had captivated people in the past, silk commands considerable attention in this day and age because of its strength, elasticity, and biochemical properties. The novel material features of silks have recently been extended due to insights into self-assembly and the role of water in assembly. These insights, in turn, have led to new processing methods to generate hydrogels, ultrathin films, thick films, conformal coatings, three dimensional porous matrices, solid blocks, nanoscale diameter fibers, and large diameter fibers.

Silk-based materials achieve their impressive mechanical properties with natural physical crosslinks of thermodynamically stable protein secondary structures also known as beta sheets ($\beta$-sheets). Thus, no exogenous crosslinking reactions or post-processing crosslinking is required to stabilize the materials. The presence of diverse amino acid side chain chemistries on silk protein chains facilitates coupling chemistry to functionalize silks, such as with cytokines, morphogens, and cell binding domains. There are no known synthetic or biologically-derived polymer systems that offer this range of material properties or biological interfaces, when considering mechanical profiles, aqueous processing, ease of functionalization, diverse modes of processing, self-forming crosslinks, biocompatibility, and biodegradability.

While no other biopolymer or synthetic polymer can match the range of features outlined above for silk, some other polymers that exhibit various properties similar or analogous to silk have been identified by the inventors of the present invention. In particular, other natural biopolymers including chitosan, collagen, gelatin, agarose, chitin, polyhydroxyalkanoates, pullan, starch (amylose amylopectin), cellulose, hyaluronic acid, and related biopolymers, or a combination thereof, have been identified. In view of the above noted features of biopolymers and of silk in particular, the present invention provides various novel nanopatterned biopolymer optical devices and methods for manufacturing such devices.

In accordance with one aspect of the present invention, one method of manufacturing a biopolymer optofluidic device includes providing a biopolymer, processing the biopolymer to yield a biopolymer matrix solution, providing a substrate, casting the biopolymer matrix solution on the substrate, embedding a channel mold in the biopolymer matrix solution, drying the biopolymer matrix solution to solidify a biopolymer optofluidic device, and extracting the embedded channel mold to provide a fluidic channel in the solidified biopolymer optofluidic device.

In accordance with one embodiment, the method optionally includes annealing the solidified biopolymer optofluidic device, and an additionally drying the annealed biopolymer optofluidic device in a vacuum environment or in a water vapor environment, or in both environments. In the preferred embodiment, the substrate is a template for an optical device, and the channel mold is a glass fiber. The channel mold may be embedded in the biopolymer matrix solution after the biopolymer matrix solution is cast, or suspended over the substrate, and the biopolymer matrix solution cast around the channel mold.

In one embodiment, the biopolymer may be silk and the biopolymer matrix solution is an aqueous silk fibroin solution having approximately 1.0 wt % to 30 wt % silk, inclusive, for example, 8.0 wt % silk. In other embodiments, the biopolymer may be chitosan, collagen, gelatin, agarose, chitin, polyhydroxyalkanoates, pullan, starch (amylose amylopectin), cellulose, hyaluronic acid, and related biopolymers, or a combination thereof. In addition, in another embodiment, the method may also include embedding an organic material in the biopolymer optofluidic device, for instance, by adding an organic material into the biopolymer matrix solution. The added organic material may be red blood cells, horseradish peroxidase, phenolsulfonphthalein, nucleic acid, a dye, a cell, an antibody, enzymes, for example, peroxidase, lipase, amylose, organophosphate dehydrogenase, ligases, restriction endonucleases, ribonucleases, DNA polymerases, glucose oxidase, laccase, cells, viruses, proteins, peptides, small molecules, drugs, dyes, amino acids, vitamins, antioxidants, DNA, RNA, RNAi, lipids, nucleotides, aptamers, carbohydrates, chromophores, light emitting organic compounds such as luciferin, carotenes and light emitting inorganic compounds, chemical dyes, antibiotics, antifungals, antivirals, light harvesting compounds such as chlorophyll, bacteriorhodopsin, protorhodopsin, and porphyrins and related electronically active compounds, or a combination thereof.

Other materials may be embedded in the biopolymer or in the biopolymer matrix solution instead of, or in addition to, organic materials, depending upon the type of optofluidic device desired.

In accordance with another aspect of the present invention, an optofluidic device made of a biopolymer and having a channel therein for conveying fluid. The optofluidic device may be a lens, a microlens array, an optical grating, a pattern generator, or a beam reshaper. In one embodiment, the optofluidic device may include a nanopatterned surface thereon.

Preferably, the biopolymer is silk, chitosan, collagen, gelatin, agarose, chitin, polyhydroxyalkanoates, pullan, starch (amylose amylopectin), cellulose, hyaluronic acid, and related biopolymers, or a combination thereof. In addition, in another embodiment, the biopolymer optofluidic device includes an embedded organic material. The organic material may be red blood cells, horseradish peroxidase, phenolsulfonphthalein, nucleic acid, a dye, a cell, an antibody, enzymes, for example, peroxidase, lipase, amylose, organophosphate dehydrogenase, ligases, restriction endonucleases, ribonucleases, DNA polymerases, glucose oxidase, laccase, cells, viruses, proteins, peptides, small molecules, drugs, dyes, amino acids, vitamins, antioxidants, DNA, RNA, RNAi, lipids, nucleotides, aptamers, carbohydrates, chromophores, light emitting organic compounds such as luciferin, carotenes and light emitting inorganic compounds, chemical dyes, antibiotics, antifungals, antivirals, light harvesting compounds such as chlorophyll, bacteriorhodopsin, protorhodopsin, and porphyrins and related electronically active compounds, or a combination thereof.

These and other advantages and features of the present invention will become more apparent from the following detailed description of the preferred embodiments of the present invention when viewed in conjunction with the accompanying drawings.

BRIEF DESCRIPTION OF THE DRAWINGS

FIG. 3C is a graph showing the measured transmission of light through the biopolymer film of FIG. 3A.

FIG. 4 is a photograph showing a biopolymer optofluidic device in accordance with one example of the present invention with blue ink flowing therethrough.

FIG. 5A is a photograph of a biopolymer optofluidic device in accordance with another example of the present invention, the biopolymer optofluidic device having biologically active materials embedded therein.

FIG. 5B is an enlarged photograph of a portion of the biopolymer optofluidic device shown in FIG. 5A which more clearly shows the sensing function attained by the embedded biologically active materials.

DETAILED DESCRIPTION OF THE INVENTION

As described in detail below, optofluidic devices in accordance with the present invention have been fabricated with a cylindrical channel therein to allow conveyance of fluid therethrough using a biopolymer such as silk. As noted, biopolymer optofluidic devices generally referred to herein may incorporate various different optical devices such as lenses, diffraction gratings, photonic crystals, waveguides, and the like, that incorporate one or more fluidic channels therein to allow conveyance of fluid therethrough. In addition, the biopolymer optofluidic devices of the present invention are described herein below as being implemented with silk in view of its superior functional characteristics and processability which were noted above. In this regard, the silk utilized was silkworm silk. However, there are many different silks, including spider silk, transgenic silks, and genetically engineered silks, variants and combinations thereof and others, that may alternatively be used in accordance with the present invention to obtain a biopolymer optofluidic device.

In addition, other biodegradable polymers may be used instead of silk. For example, other biopolymers, such as chitosan, exhibit desirable mechanical properties, can be processed in water, and form generally clear films for optical applications. Other biopolymers, such as chitosan, collagen, gelatin, agarose, chitin, polyhydroxyalkanoates, pullan, starch (amylose amylopectin), cellulose, hyaluronic acid, and related biopolymers, or a combination thereof and others may alternatively be utilized in specific applications, and synthetic biodegradable polymers such as polylactic acid, polyglycolic acid, polyhydroxyalkanoates and related copolymers may also be selectively used. Some of these polymers are not as easily processed in water. Nonetheless, such polymers may be used by themselves, or in combinations with silks, and may be used in particular biopolymer optical devices.

Figure 1:
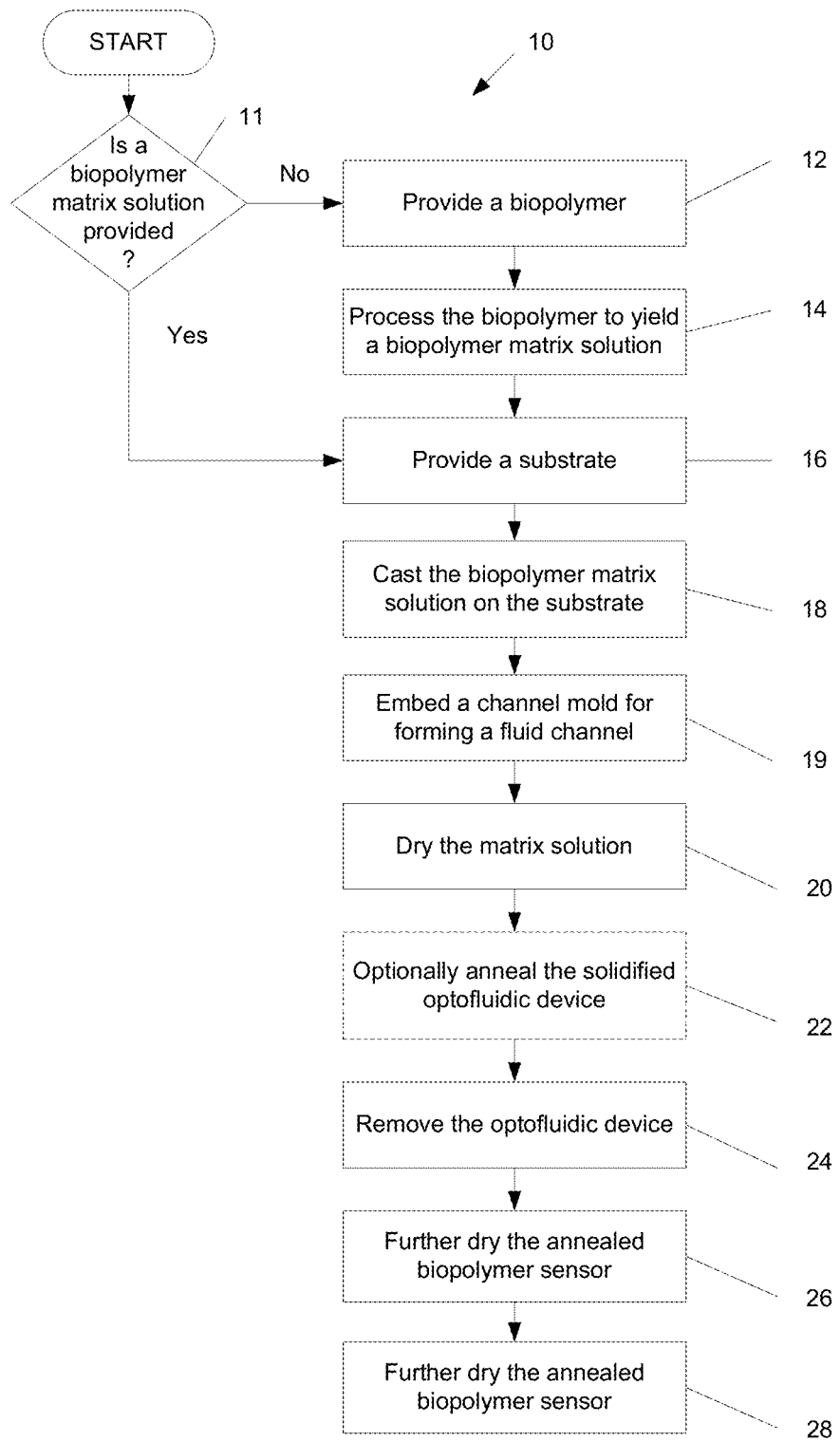
FIG. 1 is a schematic flow diagram illustrating a method in accordance with one embodiment of the present invention.

FIG. 1 is a schematic illustration of a flow diagram 10 showing a method of manufacturing a biopolymer optofluidic device in accordance with one embodiment of the present invention. If a biopolymer matrix solution is present in step 11, the process proceeds to step 16 described below. Otherwise, a biopolymer is provided in step 12. In the example where the biopolymer is silk, the biopolymer may be attained by extracting sericin from the cocoons of *Bombyx mori*. The provided biopolymer is processed to yield a biopolymer matrix solution in step 14. In one preferred embodiment, the biopolymer matrix solution is an aqueous matrix solution. However, in other embodiments, different solvents other than water, or a combination of water and other solvents, may be used, depending on the biopolymer used.

Thus, in the example of silk, an aqueous silk fibroin solution is processed in step 14, for example, 8.0 wt % silk concentration, which is then used to manufacture the biopolymer optofluidic device. Of course, in other embodiments, the concentrations may also be varied from very dilute (approximately 1 wt %) to very high (up to 30 wt %) using either dilution or concentration, for example, via osmotic stress or drying techniques. In this regard, other embodiments may utilize different percent weight solutions to optimize flexibility or strength of the resultant biopolymer optofluidic device, depending on the application. Production of aqueous silk fibroin solution is described in detail in WIPO Publication Number WO 2005/012606 entitled "Concentrated Aqueous Silk Fibroin Solution and Uses Thereof".

A substrate is provided in step 16 to serve as a mold in manufacturing the biopolymer optofluidic device. The aqueous biopolymer matrix solution is cast on the substrate in step 18. A channel mold for forming a fluid channel in the biopolymer optofluidic device is embedded in the cast aqueous biopolymer matrix solution in step 19 so that the aqueous biopolymer matrix solution surrounds the channel mold. In this regard, various fibers or lines can be used as the channel mold, such as lines made of nylon, polyethylene, Dacron® and Dyneema® ultra high molecular weight polyethylene (UHMWPE). In one embodiment, the channel mold may be a flexible glass fiber that is coated with a surfactant solution. In another embodiment of the present invention, the channel mold may be a flexible glass fiber without a wetting agent, depending upon the interfacial tension between the solution and the channel mold. The aqueous biopolymer matrix solution is then dried in step 20 to transition the aqueous biopolymer matrix solution to the solid phase. In this regard, the aqueous biopolymer matrix solution may be dried for a period of time such as 24 hours, and may optionally be subjected to low heat to expedite drying of the aqueous biopolymer matrix solution. Upon drying, a solidified biopolymer optofluidic device is formed on the surface of the substrate with the channel mold embedded therein.

Once the solvent of the biopolymer matrix solution has evaporated, the solidified biopolymer optofluidic device may optionally be annealed in step 22. This annealing step may be performed within a water vapor environment, such as in a chamber filled with water vapor, for different periods of time depending on the material properties desired. Typical annealing time periods may range from between two hours to two days, for example, and may also be performed in a vacuum environment. The annealed biopolymer optofluidic device is then removed from the substrate in step 24 and allowed to dry further in step 26. The embedded channel mold is subsequently extracted in step 28, such extraction being facilitated by the reduced surface tension provided by the surfactant coating of the glass fiber as discussed above.

In accordance with an alternative embodiment of the method, the cylindrical channel may be formed in the optofluidic device by first suspending the channel mold over the substrate, and then casting the aqueous biopolymer matrix solution to surround the channel mold. Correspondingly, upon drying of the aqueous biopolymer matrix solution and extraction of the channel mold, a solidified optofluidic device which has a channel therein can be readily fabricated.

The above described methods for fabricating an optofluidic device can be enhanced to provide additional features and functions. For instance, the substrate upon which the aqueous biopolymer matrix solution is cast may be a template for an optical device with surface features so that the resultant optofluidic device is provided with a patterned optical surface thereon. For instance, the substrate may be patterned for a diffraction grating, a lens, or the like, to allow use of the optofluidic device as a lens, optical grating, pattern generator, beam reshaper, and the like.

Figure 2:
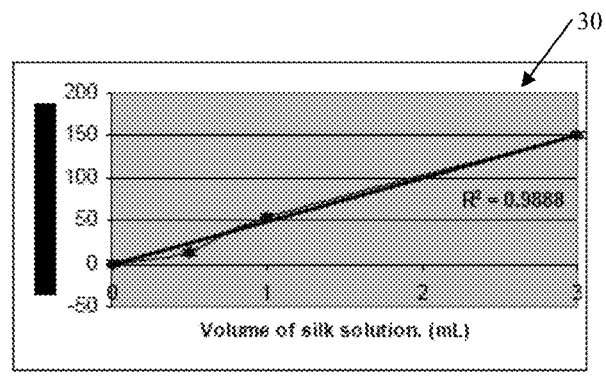
FIG. 2 is a graph that illustrates the relationship between the volume of 8% silk concentration vs. film thickness.

Experiments were conducted to validate the above-described method by manufacturing biopolymer optical devices and optofluidic devices. The relationship between the volume of 8 wt % silk concentration aqueous silk fibroin solution, and the resulting silk film thickness, is shown in the graph 30 of FIG. 2, where the aqueous silk fibroin solution was cast over a substrate surface of approximately 10 square centimeters. The X-axis shows the volume of silk fibroin solution in mL, and the Y-axis shows the thickness of the resultant film in μm.

Of course, the film properties such as thickness and biopolymer content, as well as optical features, may be altered based on the concentration of fibroin used in the process, the volume of the aqueous silk fibroin solution deposited, and the post deposition process for drying the cast solution to lock in the structure. Accurate control of these parameters is desirable to ensure the optical quality of the resultant biopolymer optofluidic device and to maintain various characteristics of the biopolymer optofluidic device, such as transparency, structural rigidity, and flexibility. Furthermore, additives to the biopolymer matrix solution may be used to alter features of the biopolymer optofluidic device such as morphology, stability, and the like, as known with polyethylene glycols, collagens, and the like.

Figure 3A:
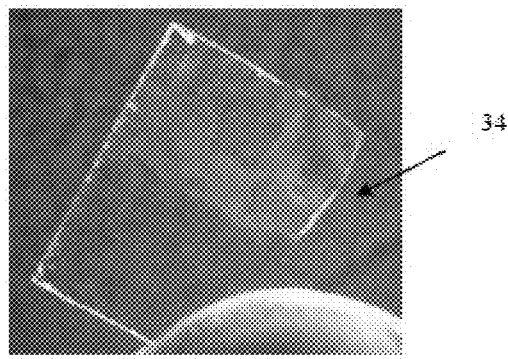
FIG. 3A is a photograph of a biopolymer film made of silk.
Figure 3B:
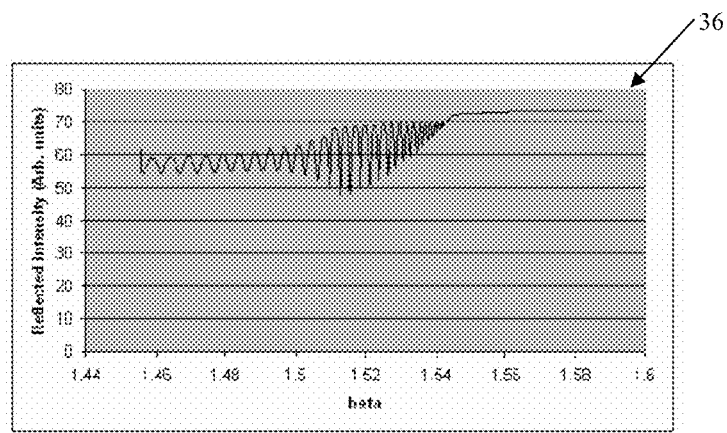
FIG. 3B is a graph showing the prism coupled angular dependence of reflectivity of the biopolymer film of FIG. 3A.

An unpatterned biopolymer film having a thickness of 10 μm was manufactured in the above-described manner using an aqueous silk fibroin solution, and was characterized in a scanning prism coupled reflectometer from Metricon Corporation. FIG. 3A illustrates the unpatterned biopolymer film 34 manufactured and characterized. The index of refraction of the biopolymer film 34 was measured to be n=1.55 at 633 nm, which is slightly higher than the index of refraction of conventional borosilicate glass. The measured index of refraction confirms that the value is high enough to afford reasonable contrast for optical use such as in air-silk biophotonic crystals (BPC) ($\Delta n_{fibroin} - \Delta n_{air} = 0.55$). The characterization of the unpatterned silk film 34 is shown in graph 36 of FIG. 3B which clearly demonstrates the prism coupled angular dependence of the reflectivity. The oscillations in graph 36 are due to coupling into guided waves, demonstrating the use of silk as a waveguide material.

In addition, the unpatterned silk film 34 was also analyzed to determine transparency. FIG. 3C is a graph 38 that illustrates the measured transmission of light through the silk film 34 in various wavelengths. Transmission measurements indicate that the unpatterned silk film 34 was highly transparent across the visible spectrum. For comparison, similar thickness films were also cast in collagen, and polydimethylsiloxane (PDMS). The free-standing structural stability was found to be inferior, and the resultant biopolymer optical device was not self-supporting when implemented as a thin film. However, such biopolymers may be used in other applications if structural stability is deemed to be not as important.

Importantly, shaped films having various thicknesses have been patterned on the nanoscale using the method of FIG. 1 described above. In particular, the aqueous solution of silk fibroin was cast onto specific substrates with patterns thereon. The substrate surfaces may be coated with Teflon™ to ensure even detachment after the biopolymer matrix solution transitions from the liquid to the solid phase. The ability of the biopolymer casting method of the present invention for forming highly defined nanopatterned structures was verified by casting diffraction gratings and lenses. Regular patterned features with dimensions down to 210 nm, and localized surface roughness of less than 20 nm, have been attained.

The measured roughness of cast silk film on an optically flat surface shows measured root mean squared roughness values between 2.5 and 5 nanometers, which implies a surface roughness easily less than λ/50 at a wavelength of 633 nm. Atomic force microscope images of patterned silk diffractive optics show the levels of microfabrication obtainable by casting and lifting silk films off of appropriate molds. The images show definition in the hundreds of nanometer range and the sharpness of the corners indicates the possibility of faithful patterning down to the tens of nanometers.

With silk matrices and films demonstrated to have such structural stability and favorable optical properties as discussed above, the technological field of microfluidic devices, as well as the technological field of optofluidics can be extended so that the optofluidic devices can be manufactured as described using biopolymers such as silk and other materials. Optofluidic devices of the present invention avoid the inorganic polymer matrices required in which the network of liquids necessary are flowed and allow realization of microchannels through the biopolymer, such as silk, that define channels and reservoirs.

FIG. 4 is a photograph showing a biopolymer optofluidic device 50 in accordance with one example of the present invention, which was manufactured using the method described above relative to FIG. 1. The specific biopolymer used was silk. Fluid channels 54, 55 were formed in the optofluidic device 50 by casting the biopolymer matrix solution, embedding glass fibers therein, curing the biopolymer matrix solution, and subsequently extracting the glass fibers. In this regard, in the illustrated example, 125 micron diameter glass fibers were used. FIG. 4 further shows blue liquid ink flowing through one of the channels 55 of the optofluidic device 50, the ink being injected using a syringe 58.

Of course, in other embodiments, different diameter glass fibers may be used, depending on the desired size of the channel and fluid flow characteristics therethrough. For instance, the diameter of the glass fiber may be as small as 50 microns or as large as 250 microns. In addition, different diameter glass fibers may be used in fabrication of a single optofluidic device so as to provide fluid flow channels having different flow capacities and characteristics. Further, soft lithography techniques may also be used where fluidic channels may be designed on a mask, the silk biopolymer material may be cast, the glass fibers embedded, and the silk biopolymer material detached, thereby leaving a microchannel behind.

A significant advantage of the biopolymer optofluidic devices in accordance with the present invention is the ability for the optofluidic devices to be biologically activated by embedding organic materials since they are entirely organic and biocompatible. The water-based processing that can be used, for example, for silk optofluidic devices, increases cellular survivability of embedded organic materials and likelihood of biocompatibility. Varying degrees of functionalization can be performed making both fluids and light interactive to attain a novel class of biopolymer optofluidic devices such as sensors that will increase sensitivity, detectability, and selectivity.

In other words, the optofluidic devices of the present invention can be biologically activated by embedding organic materials, such as proteins. This allows biologically induced changes to the biopolymer optofluidic device, which alters local optical characteristics of the biopolymer optofluidic device. The variation in the optical characteristics can function as an indicator of the changes occurring at the biological level. Such responsive biopolymer optofluidic devices can be implemented by the addition of proteins, peptides, nucleic acid (such as RNA and/or DNA), enzymes, protein complexes, viruses, cells, antibodies, other biomolecules, dyes or other compounds such as red blood cells, horseradish peroxidase, and phenolsulfonphthalein, other cells, tissues or other living materials, a nucleic acid, a dye, a cell, an antibody, as described further in Appendix I, enzymes, for example, peroxidase, lipase, amylose, organophosphate dehydrogenase, ligases, restriction endonucleases, ribonucleases, DNA polymerases, glucose oxidase, laccase, cells, viruses, bacterias, proteins, peptides for molecular recognition, small molecules, drugs, dyes, amino acids, vitamins, antioxidants, plant cells, mammalian cells, and the like, DNA, RNA, RNAi, lipids, nucleotides, aptamers, carbohydrates, optically-active chromophores including beta carotene or porphyrins, light emitting organic compounds such as luciferin, carotenes and light emitting inorganic compounds, chemical dyes, antibiotics, yeast, antifungals, antivirals, and complexes such as hemoglobin, electron transport chain coenzymes and redox components, light harvesting compounds such as chlorophyll, phycobiliproteins, bacteriorhodopsin, protorhodopsin, and porphyrins and related electronically active compounds, or a combination thereof.

It should be appreciated that in other embodiments these compounds may be used to coat the surface of the optofluidic device. However, embedding such materials may be preferable since coatings can be more easily removed. As indicated above, other materials may also be embedded in the polymer or in the biopolymer matrix solution instead of, or in addition to, organic materials depending upon the type of optofluidic device desired.

As an example, FIGS. 5A and 5B show photographs of a biopolymer optofluidic device 70 in accordance with still another embodiment of the present invention. As shown, the biopolymer optofluidic device 70 includes channels 74 for conveying fluid therethrough. The channels 74 were fabricated by casting a silk fibroin solution on a substrate and embedding 125 micron diameter glass fibers that served as the channel molds. These glass fibers were extracted upon curing of the silk fibroin solution as described relative to the method shown in FIG. 1. The silk fibroin solution cast was doped with phenol red so that the resultant biopolymer optofluidic device 70 is functionalized to allow pH detection of the fluid that flows in the channels 74. Correspondingly, in the channels 74 of the biopolymer optofluidic device 70, the flow of a basic, neutral, or acid solution induces a color change in the channels 74.

More specifically, an 8% silk fibroin solution was combined with the pH indicator phenol red to provide a 1 mg/ml concentration of the pH indicator in the aqueous biopolymer matrix solution. A volume of 1.5 ml of the phenol red/silk solution was then cast into a 7 $cm^2$ square substrate. A surfactant solution was used to coat three 150 micron diameter optical fibers. These surfactant coated glass fibers were then placed next to each other within the bulk volume of the silk fibroin solution. The silk fibroin solution was then allowed to dry overnight to form the solidified optofluidic device, and the device was annealed in the presence of vacuum and water vapor for two hours.

The solidified optofluidic device was removed and a dilute NaOH solution with a pH=8 was flowed through one of the functionalized channels 74. The channel turned pink color upon flow of the NaOH solution. As also shown in the enlarged photograph of FIG. 5B, a small amount of NaOH solution remaining in the channel 74 through which NaOH solution was flowed is clearly visible and can be detected based on the pink coloration (not shown) within the otherwise amber colored (not shown) channel 74. As can be appreciated, the remaining base solution in the channel will be easily identifiable due to the color change in the optofluidic device 70. Again, this different coloration resulted from the pH of the NaOH solution, thereby allowing the optofluidic device of the present invention to provide additional function which is not attainable in conventional optofluidic devices.

Furthermore, as noted previously, additional optical functionalization of the optofluidic devices in accordance with the present invention can be attained by forming diffractive or refractive optical features on the surface of the optofluidic device 70. In particular, the aqueous biopolymer matrix solutions can be cast onto an optical element that serves as a substrate thereby forming the optical features such as a nanopatterning on the surface of the optofluidic device. The substrate surfaces may be coated with Teflon™ to ensure even detachment after the aqueous biopolymer matrix solution transitions from the liquid to the solid phase. Thus, as noted, the optofluidic device may be lenses, microlens arrays, optical gratings, pattern generators, beam reshapers or other devices that have channels therein for allowing fluid to flow therethrough.

The ability to fabricate optical materials and waveguides in biopolymers, such as silk, enables a new class of optical devices to be created by bringing together the mature and diverse methodologies of optical physics and the versatility of a biological substrate. As described, the material properties of silk films are ideal for patterning on the nanoscale using casting techniques on patterned surfaces. With appropriate relief masks, silk films can be processed into versatile optical elements. The advantages of this approach combines (a) the nature of the silk films which is organic, controllably degradable, biocompatible, structurally strong; (b) the power of diffractive and transmissive optics embedded in the organic matrix; and (c) the creation of biologically active optical elements. The process explained above allows the formation of highly defined patterned structures on the nanoscale in production of bio-optical biopolymer devices.

The structural stability and ability to faithfully reproduce nanostructure makes the above described method appropriate for manufacture of many different diffractive optical structures or refractive micro and nano-optical structures using biopolymers such as silk. Among the optical elements that can be readily made are silk gratings as described above, silk micro and nano lens arrays, silk pattern generators, silk beam diffusers, and silk beam homogenizers, these optical elements having been demonstrated in silk.

The above noted attributes of the biopolymer devices in accordance with the present invention also allows manufacture of a biocompatible, low-cost, organic based solar energy systems that include solar cell elements based on biopolymers such as layered silk optics and silk films. A layered biopolymer structure such as silk matrices or other appropriate biopolymer matrices may be tailored for use as solar panels and solar cells. Such matrices may then be used in conjunction with light harvesting compounds for efficient harnessing and storage of energy in sunlight.

Figure 6:
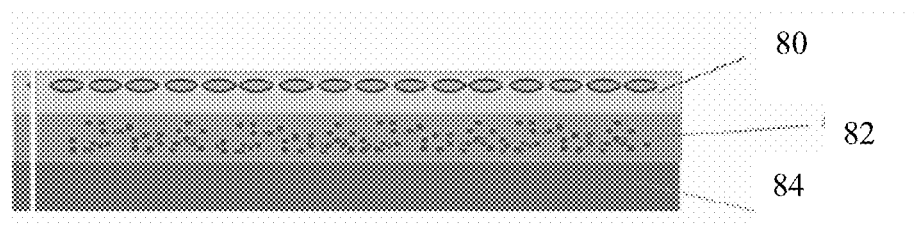
FIG. 6 is a view of a biopolymer optical device for use in a solar energy system.

FIG. 6 schematically illustrates the general structure of a biopolymer solar panel for use in a solar energy system in accordance with one example of implementation. The biopolymer solar panel in one example embodiment includes (1) a microlens array 80 with suitably patterned refractive silk optical elements which enhances and localizes the collection of light, and preferably focus it on the bottom layer of the system; (2) a light harvesting layer 82 doped with light harvesting compounds (such as chloroplasts, rhodopsin, bacteriorhodopsin, phycobiliproteins and related light adsorbing compounds or green plant components) which serves as the light collector and energy storage device; and (3) an electrical interface layer 84, which transfers the energy stored to appropriate circuitry and subsystems that interfaces with the biopolymer solar panel. The electrical interface layer may be formed via traditional sputter coatings, or via green chemistry methods using tyrosine wires integrated with the silk.

Antibody Stability in Silk Films

Materials—Anti-IL-8 monoclonal antibody (IgG1) was purchased from eBioscience, Inc. human polyclonal antibody IgG and human IgG ELISA Quantitation Kit were purchased from Bethyl Laboratories Inc. All other chemicals used in the study were purchased from Sigma-Aldrich (St. Louis, MO).

Antibody entrapment in silk films - human polyclonal antibody IgG—Ten ml 1mg/m1 IgG mixed with 167 ml 6% silk solution make the IgG concentration in silk film mg/g silk. 100 µl of mixed IgG solution was added to each well of 96 well plate which was placed in a fume hood with cover opened overnight. The dried film was either treated or not treated with methanol. For methanol treatment, the wells were immersed in 90% methanol solution for 5 min and dried in the fume hood. All dry 96 well plates were then stored at 4° C., room temperature, and 37° C.

Anti-IL-8 monoclonal antibody (IgG1)—0.5m1 1 mg/ml IgG1 mixed with 83 ml 6% silk solution make the IgG1 concentration in silk film 0.1 mg/g silk. 50 µl of mixed IgG1 solution was added to a well of 96 well plate which was placed in a fume hood with cover opened overnight. The dried film was either treated or not treated with methanol. For methanol treatment, the wells were immersed in 90% methanol solution for 5 min and dried in the fume hood. All dry 96 well plates were then stored at 4° C., room temperature, and 37° C.

Antibody measurement—Five wells prepared at the same condition were measured for statistic. Pure silk (without antibody) was used as a control.

For non methanol-treated samples, 100 µl of PBS buffer, pH 7.4, was added to the well which was further incubated at room temperature for 30 min to allow the film to completely dissolve. Aliquot of solution was then subjected to antibody measurement. For methanol-treated samples, 100 µl HFIP was added into each well which was further incubated at room temperature for 2 hours to allow the film completely dissolve. The silk HFIP solution was dried in a fume hood overnight. The follow step was the same as non methanol-treated samples, added PBS buffer and pipette the solution for antibody measurement.

Figure 7:
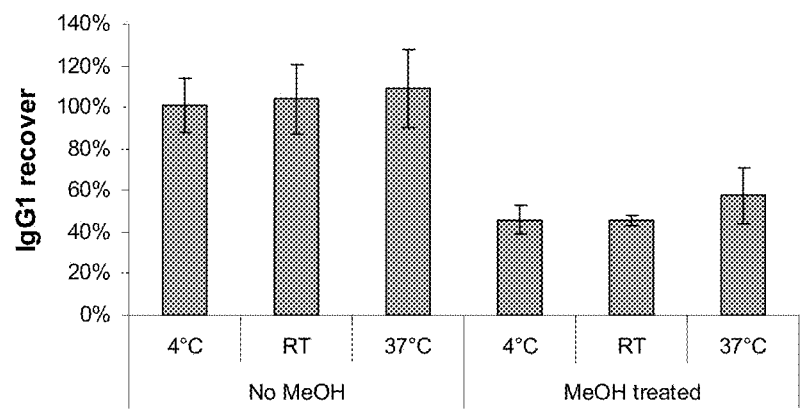
FIG. 7 is absorbance data for antibody IgG1 activity related to initial activity in the silk films prepared in the two different formats and stored at the three different temperatures.
Figure 8:
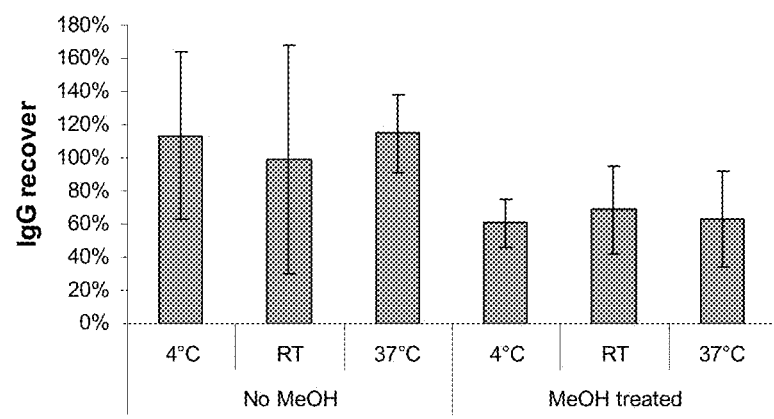
FIG. 8 is absorbance data for antibody IgG activity related to initial activity in the silk films prepared in the two different formats and stored at the three different temperatures.

ELISA—Polystyrene (96-well) microtitre plate was coated with 100 µL of antigen anti-Human IgG-affinity at a concentration of 10 µg/mL prepared in antigen coating buffer (bicarbonate buffer, 50 mM, pH 9.6) and then incubated overnight storage at room temperature. The wells were then washed three times with TBS-T buffer. The unoccupied sites were blocked with 1% BSA in TBS (200 µL, each well) followed by incubation for 30 minutes at room temperature. The wells were then washed three times with TBS-T. The test and control wells were then diluted with 100 µL. of serially diluted serum. Each dilution was in TBS buffer. Serially diluted blanks corresponding to each dilution were also present. The plate was then incubated for 1 h at room temperature. The plate was washed again with TBS-T buffer (five times). Bound antibodies were assayed with an appropriate conjugate of anti-human IgG-HRP (1:100,000), 100 µL of it was coated in each well and kept at room temperature for 1 hour. Washing of the plate with TBS-T (five times) was followed by addition of 100 µl , TMB in each well and incubation at room temperature for 5-20 min. The absorbance of each well was monitored at 450 nm on a VersaMax microplate reader (Molecular devices, Sunnyvale, CA). FIG. 7 shows antibody IgG1 activity related to initial activity in the silk films prepared in the two different formats and stored at the three different temperatures. FIG. 8 shows antibody IgG activity related to initial activity in the silk films prepared in the two different formats and stored at the three different temperatures.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

The foregoing description of the aspects and embodiments of the present invention provides illustration and description, but is not intended to be exhaustive or to limit the invention to the precise form disclosed. Those of skill in the art will recognize certain modifications, permutations, additions, and combinations of those embodiments are possible in light of the above teachings or may be acquired from practice of the invention. Therefore, the present invention also covers various modifications and equivalent arrangements that fall within the purview of the appended claims.

What is claimed is:

1. A device made of a solidified silk fibroin matrix, comprising:
    at least one fluidic channel therein;
    an embedded organic material; and
    at least one optical feature,
    wherein the silk fibroin is from at least one of silkworm silk, spider silk, genetically engineered silk, synthetic silk, or combinations thereof,
    wherein the device is characterized in that when a fluid flows through the at least one fluidic channel, it interacts with the embedded organic material to alter at least one local optical property of the solidified silk fibroin matrix such that the device is biologically and optically active, and
    wherein the at least one local optical property is selected from the group consisting of diffractive property, refractive property, transmissive property, and combinations thereof.

2. The device of claim 1, wherein the at least one optical feature is at least one of a lens, a microlens array, an optical grating, a pattern generator, and a beam reshaper.

3. The device of claim 1, wherein a surface of said device comprises features formed in a pattern thereon.

4. The device of claim 1, wherein said solidified silk fibroin matrix further comprises a biopolymer selected from the group consisting of: chitosan, collagen, gelatin, agarose, chitin, polyhydroxyalkanoates, pullan, starch, amylose, amylopectin, cellulose, hyaluronic acid, and combinations thereof.

5. The device of claim 1, wherein said organic material is selected from the group consisting of red blood cells, horseradish peroxidase, phenolsulfonphthalein, and combinations thereof.

6. The device of claim 1, wherein said organic material is selected from the group consisting of a nucleic acid, a dye, a cell, an antibody, enzymes, peroxidase, lipase, amylose, organophosphate dehydrogenase, ligases, restriction endonucleases, ribonucleases, DNA polymerases, glucose oxidase, laccase, cells, viruses, proteins, peptides, small molecules, drugs, dyes, amino acids, vitamins, antioxidants, DNA, RNA, RNAi, lipids, nucleotides, aptamers, carbohydrates, chromophores, light emitting organic compounds, luciferin, carotenes and light emitting inorganic compounds, antibiotics, antifungals, antivirals, light harvesting compounds, bacteriorhodopsin, protorhodopsin, porphyrins, electronically active compounds, or combinations thereof.

7. The device of claim 1, wherein the at least one channel is a microchannel.

8. A method of forming the device of claim 1, comprising steps of:
    providing a substrate;
    casting a silk fibroin solution on the substrate;
    embedding a channel mold in the silk fibroin solution;
    solidify said silk fibroin solution; and extracting the embedded channel mold thereby forming the device made of the solidified silk fibroin matrix.

9. The method of claim 8, wherein the silk fibroin solution contains approximately 1.0 wt % to 30 wt % silk fibroin.

10. The device of claim 3, wherein the patterned features on the surface of the device have a localized surface roughness below 20 nm.

11. The device of claim 1, wherein a surface of the device comprises features patterned to form a microlens array characterized in that when the device exposed to incident light, the microlens array localizes the light below the surface of the device, and wherein the embedded organic material is or comprises light harvesting compounds that collect light and store energy.

* * * * *